United States Patent [19]
Peter et al.

[11] Patent Number: 6,124,373
[45] Date of Patent: Sep. 26, 2000

[54] BONE REPLACEMENT COMPOUND COMPRISING POLY(POLYPROPYLENE FUMARATE)

[75] Inventors: Susan J. Peter, Baltimore, Md.; Michael J. Yaszemski, Rochester, Minn.; Antonios G. Mikos, Houston, Tex.

[73] Assignee: WM. Marsh Rice University, Houston, Tex.

[21] Appl. No.: 09/289,361

[22] Filed: Apr. 9, 1999

Related U.S. Application Data

[60] Provisional application No. 60/081,308, Apr. 10, 1998, provisional application No. 60/082,182, Apr. 16, 1998, and provisional application No. 60/081,405, Apr. 10, 1998.

[51] Int. Cl.$^7$ ........................................ C08L 67/06
[52] U.S. Cl. .................. 523/116; 523/113; 524/539; 528/272; 424/78.31; 424/423; 424/426
[58] Field of Search ..................... 523/113, 116; 524/539; 528/272; 424/78.31, 423, 426

[56] References Cited

U.S. PATENT DOCUMENTS

| | | | |
|---|---|---|---|
| 5,286,763 | 2/1994 | Gerhart et al. | 523/113 |
| 5,644,005 | 7/1997 | Suggs et al. | 524/539 |
| 5,733,951 | 3/1998 | Yaszemski et al. | 523/116 |

*Primary Examiner*—Andrew E. C. Merriam
*Attorney, Agent, or Firm*—Conley, Rose & Tayon, P.C.

[57] ABSTRACT

A method for controlling the gel point of a bone cement containing poly(polypropylene fumarate), a cross-linking monomer, an initiator, an inorganic filler, and a radical initiator. The gel point is controlled by varying the molecular weight of the poly(polypropylene fumarate) while maintaining the weight average molecular weight ($M_w$) of the poly(polypropylene fumarate) above 2000 and the polydispersity index of the poly(polypropylene fumarate) below 2. In a preferred embodiment, the molecular weight of the poly(polypropylene fumarate) greater than 4000, and more preferably greater than 5000.

20 Claims, 9 Drawing Sheets

Poly(Propylene Fumarate)

BONE REPLACEMENT COMPOUND COMPRISING POLY(POLYPROPYLENE FUMARATE)

CROSS-REFERENCE TO RELATED APPLICATIONS

The present application claims the benefit of provisional applications Ser. No. 60/081,308, filed Apr. 10, 1998 and entitled Synthesis of Poly(Proplyene Fumarate) by Acylation of Propylene Glycol in the Presence of a Proton Scavenger; Ser. No. 60/082,182, filed Apr. 16, 1998 and entitled In Vivo Degradation of a Poly(Propylene Fumarate)/ β-Tricalcium Phosphate Injectable Composite Scaffold; and Ser. No. 60/081,405, filed Apr. 10, 1998 and entitled Crosslinking Characteristics of an Injectable Poly(Propylene Fumarate)/ β-Tricalcium Phosphate Past and Mechanical Properties of the Crosslinked Composite for Use as a Biodegradable Bone Cement.

STATEMENT REGARDING FEDERALLY SPONSORED RESEARCH OR DEVELOPMENT

This work was funded by the National Institutes of Health (R01-AR44381) (AGM), the National Science Foundation (PSE), and National Institutes of Health Biotechnology Training Grant 5T32GM08362.

TECHNICAL FIELD OF THE INVENTION

This invention relates to a compound for replacing or reconstructing living bone. More particularly, the present invention relates to a compound comprising a high molecular weight poly(polypropylene fumarate) component, a porogen, a cross-linking agent, an inorganic filler, and a radical initiator, in which the relative amounts of each component are optimized for use in surgical bone replacement.

BACKGROUND OF THE INVENTION

It is often desired to replace or reconstruct all or a portion of a living bone, such as when a bone has been broken or has been resected as a result of a bone tumor. In these instances, the missing bone can be replaced with a mechanical device, such as a pin, plate or the like, or it can be replaced with an implant that is designed to more closely resemble the original bone itself. Often these implants comprise biodegradable compounds or parts made from such compounds. For example, it is known to provide porous, biodegradable compounds that contain or are coated with an osteogenic substance. It is contemplated that bone tissue will grow back into the pores of the implant and will gradually replace the entire implant as the implant itself is gradually degraded in the in vivo environment.

For obvious reasons, implants should be biocompatible and non-toxic. Furthermore, the steps required for implantation of the implant (eg. the application or generation of heat and the generation of chemical by-products) should also be biocompatible and non-toxic. For example, the generation of extreme heat or lethal temperatures can cause necrosis of the tissue surrounding the implant site. Also, the techniques and time periods required for implantation should be suited to the surgical environment.

Under current practices, bone implants are typically formed from a substance that is initially malleable and then becomes hard after a reasonably short period of time. The time required for the bone replacement compound to become fully cross-linked (i.e. its gel point) should be long enough to allow positioning and manipulation by the surgeon and short enough to ensure that the compound has hardened before surgery is complete. A desirable gel point is typically in the range of from about 1 minute to about 120 minutes and more preferably between about 5 and about 60 minutes. In addition, it is often desirable to be able to select or control the gel point, so that the gel point can be optimized for a given surgical situation.

In addition, because living bone tends to atrophy and degrade in the absence of compressive stress, it is important that the implant not become too hard. An implant whose compressive strength is too great (i.e. an implant that is too hard) will cause stress shielding of the surrounding bone. Stress shielding in turn weakens the surrounding bone and may ultimately result in catastrophic failure. Normal human trabecular bone has an average compressive strength of approximately 5 MPa and modulus of elasticity of approximately 50 MPa Conventional bone cements are formed of poly(methylmethacrylate) (PMMA) or poly (methylmethacrylate-co-styrene). The compressive strength of these bone cements is approximately 100 MPa. This is much higher than the mid-range for trabecular bone (5 MPa), and is of the same order of magnitude as the mid-range compressive strength for compact bone. The much greater compressive strength of prior art bone cements can lead to stress shielding and loss of adjacent bone. Other disadvantages of known bone cements include that they are not degradable, and continually accumulate fatigue damage as they are loaded, which sometimes leads to structural failure.

Hence, the suitability of a given substance for implantation as a bone replacement depends on its biocompatibility, set time, biodegradability and compression strength. Certain polymers have been found to be suitable in this regard.

Poly(propylene fumarate) (hereinafter "T(PF)") is one such substance. P(PF) is an unsaturated linear polyester that degrades in the presence of water into propylene glycol and fumaric acid, degradation products which are cleared from the human body by normal metabolic processes. Although P(PF) has been previously known, its routine, reproducible synthesis and the synthesis of high molecular weight forms and forms with low polydispersity indices have not previously been successfully accomplished. Because the fumarate double bonds in P(PF) are reactive and crosslink at low temperatures, it has potential to be an effective in situ polymerizable biomaterial. U.S. Pat. No. 5,733,951 discloses a composite mixture incorporating P(PF), a crosslinking monomer (N-vinyl pyrrolidinone), a porogen (sodium chloride), and a particulate phase (β-tricalcium phosphate) that can be injected or inserted into skeletal defects of irregular shape or size. The '951 patent does not disclose any method for controlling either gel time or the heat released during cross-linking. Hence, it is further desirable to provide a P(PF) composition wherein the heat released is minimized and the gel time is controllable, without adversely affecting the mechanical properties of the final product.

BRIEF SUMMARY OF THE INVENTION

The present invention provides a method for making a P(PF)-based bone cement wherein the heat released is minimized and the gel time is controllable, while the mechanical properties of the final product are maintained in a desired range. The present invention uses a high molecular weight linear poly(propylene fumarate) having a low polydispersity index, or PI ($PI=M_w/M_n$ where $M_w$ is the weight average molecular weight and $M_n$ is the number average molecular weight). According to the present invention, this high molecular weight linear P(PF) is mixed with a cross-linking agent, a radical initiator and one or more fillers. The relative amount of each component is optimized to give a bone cement having setting properties and mechanical properties that are superior to previously known formulations.

The mechanical properties of the cured material can be tailored by altering the ratios of the porogen and particulate phase, as well as the ratio of polymer to cross-linking agent. Equally importantly, the gel point and amount of heat released can be controlled in a manner that does not affect the mechanical properties of the cured material, by varying the number average molecular weight.

BRIEF DESCRIPTION OF THE DRAWINGS

For an introduction to the detailed description of the preferred embodiments of the invention, reference will now be made to the accompanying Figures, wherein.

DETAILED DESCRIPTION OF THE PREFERRED EMBODIMENTS

Figure 1:
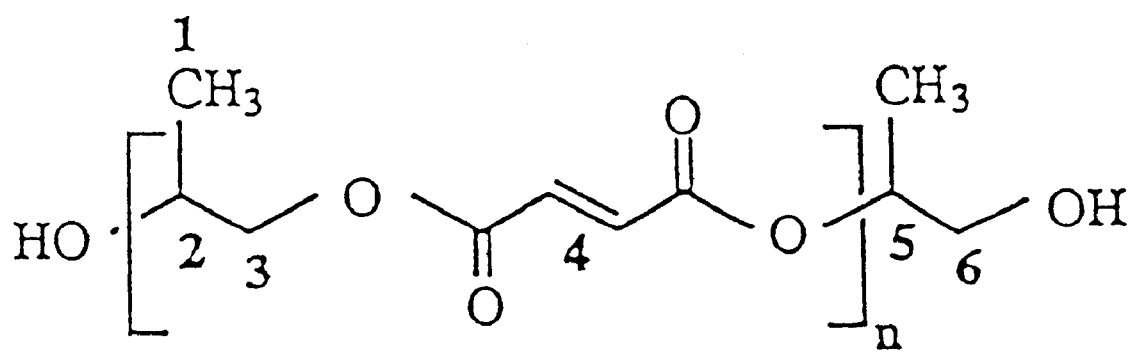
FIG. 1 is a labeled chemical structure of poly(propylene fumarate)

Referring initially to FIG. 1, the chemical structure for the desired reaction product P(PF) is shown and various functional groups are labeled 1–6. Specifically, the number 1 corresponds to the methyl functionality, the number 2 corresponds to the propyl methane, 3 corresponds to the propyl methylene of the secondary alcohol functionality, 4 corresponds to the fumarate double bond atoms, 5 corresponds to the propyl methane, and 6 corresponds to the propyl methylene of the primary alcohol functionality. A preferred method for manufacturing P(PF) with this structure having a $M_w$ of at least 4000 and a PI less than 2 is disclosed in co-pending PCT application Ser. No. PCT/US99/07912, filed concurrently herewith and entitled Synthesis Of Poly (Propylene Fumarate) By Acylation Of Propylene Glycol In The Presence Of A Proton Scavenger, which is incorporated by reference herein in its entirety.

It has been discovered that the use of high-purity, high molecular weight P(PF) has a mitigating effect on the amount of heat released during the cross-linking process and reduces the time required for the compound to set. In order to determine the effects of the composite formulation on the handling properties of the injectable paste, various formulations were tested. Specifically, the molecular weight, amount of cross-linking agent, amount of initiator, and porogen weight percent were varied according to a fractional factorial design. The effect of these parameters on the maximum crosslinking temperature, heat release upon crosslinking, and gel point were measured. In addition, the compressive strength at yield and compressive modulus of the crosslinked composites were evaluated. The precise methods of these tests are described in detail below, along with the test results.

Materials And Methods

Materials. Fumaryl chloride (Aldrich, Milwaukee, Wis.) was purified by distillation with a temperature range of 161–164° C. Propylene glycol, benzoyl peroxide, anhydrous potassium carbonate, and N-vinyl pyrrolidinone (Acros, Pittsburgh, Pa.) were used as received. Sodium chloride (Acros) was sieved to a particle size of 300–500 μm prior to use. Beta-tricalcium phosphate (β-TCP) particles (100 mesh) were obtained from DePuy (Warsaw, Ind.). All solvents used for polymer purification obtained from Fisher (Pittsburgh, Pa.) as reagent grade and used as received. Surgical Simplex® P radiopaque bone cement (control no. RKE518) was obtained from Howmedica Inc. (Rutherford, N.J.) [liquid phase: 97.4% methyl methacrylate, 2.5% N,N-dimethyl-p-toluidene, and 75 ppm hydroquinone; solid phase: 15% poly(methyl methacrylate), 75% methyl methacrylate-styrene copolymer, 10% barium sulfate] and was used as a control (hereinafter referred to as "PMMA control").

P(PF) Synthesis. P(PF) was synthesized through a two-step reaction process as described previously. Briefly, fumaryl chloride, propylene glycol, and potassium carbonate were combined at 1:3:1.5 molar ratios at 25° C. under a nitrogen atmosphere, forming a short chain oligomer. This was followed by a transesterification reaction at 160° C. and 100–110 mm Hg. The duration of this reaction determined the ultimate molecular weight of P(PF). The polymer was purified through solution-precipitation in chloroform and petroleum ether, respectively, resulting in a viscous, amber-colored product. Gel permeation chromatography was used to determine polymer molecular weight distributions through application of a differential refractometer. A Phenogel guard column (50×7.8 mm, 5 μm, mixed bed, Phenomenex, Torrance, Calif.) and a Phenogel column (300×7.8 mm, 5 μm, mixed bed, Phenomenex) were used to elute the samples at 1 ml/min chloroform flow rate. Polystyrene standards were used to obtain a calibration curve for calculating the polymer molecular weights. For the polymers used in these experiments, the transesterification reaction was run for 8 and 16 hrs, producing P(PF) of number average molecular weights ($M_n$) 2500 and 5000 Da, respectively, with each having a polydispersity index less than 2.

Experimental Design. All experiments described below were based on a Resolution III two-level fractional factorial design that entailed varying the following four parameters: 1) the molecular weight of the P(PF), 2) the amount of the cross-linking agent, N-vinyl pyrrolidinone (N-VP), 3) the amount of initiator, benzoyl peroxide (BP), and 4) the weight percent of the porogen, sodium chloride (NaCl). A high and low value was chosen for each parameter, and these levels were combined according to the fractional factorial design to create 8 composite formulations. The high and low values for all four parameters are represented in Table 1(a) below. In addition, all formulations incorporated 0.33 gμ-TCP per 1 g P(PF)

TABLE 1(a)

High and low levels for four parameters tested in a Resolution III, two-level fractional factorial design.

P(PF)

| Level | Molecular Weight | N-VP/P(PF) | NaCl Content (wt. %) | BP/P(PF) |
|---|---|---|---|---|
| High (+) | 5000 | 0.5 ml/ 1.0 g | 40 | 0.005 g/ 1.0 g |
| Low (−) | 2500 | 0.25 ml/ 1.0 g | 30 | 0.001 g/ 1.0 g |

The various permutations of high and low values that were used to create the Resolution III, two-level fractional factorial experimental design at set out in Table 1(b) below.

TABLE 1(b)

Permutations of the experimental variables in the Resolution III, two-level fractional factorial design.

| Formulation | P(PF) Molecular Weight | N-VP/P(PF) | NaCl Content (wt. %) | BP/P(PF) |
|---|---|---|---|---|
| 1 | + | + | + | − |
| 2 | + | + | − | + |
| 3 | + | − | + | + |
| 4 | + | − | − | − |
| 5 | − | + | + | + |
| 6 | − | + | − | − |
| 7 | − | − | + | − |
| 8 | − | − | − | + |

The effects of variations between high and low values for each of the four parameters on 1) the maximum temperature reached during crosslinking, 2) the total heat released during crosslinking, 3) the gel point, 4) the compressive strength and 5) the compressive modulus of the cured composites were evaluated. The results from each experiment were examined to determine the main effects of each parameter on the measured property. The experiment was designed this way in order to obtain a maximum amount of information, i.e. to demonstrate the relative effect of each parameter, while minimizing the number of trials. All experiments were completed in triplicate except for the mechanical studies, where five repetitions were used for each formulation tested.

Measurement Methods

Temperature Profiles. The temperature profile was recorded throughout the crosslinking process using a cylindrical Teflon mold suspended in a 37° C. water bath. Inner dimensions of the mold measured 10 mm in diameter and 15 mm in height; outer dimensions were 20 mm in diameter and 20 mm in height. For each of the 8 trials represented in Table 1(b), the P(PF) was dissolved in half of the N-VP required for the formulation, and the BP was dissolved in the remaining N-VP. The NaCl and β-TCP were blended with the N-VP/P(PF) solution. At time zero, the BP solution was added with rapid mixing. The paste was placed in the mold, a thermocouple (Omega, KMTSS-032U-6, Stamford, Conn.) was inserted to half the depth of the mold, and temperature readings were recorded every fifteen seconds until 2 minutes beyond the peak temperature. PMMA controls were completed in a similar manner; the solid and liquid phases of the surgical formulation were combined, placed in the mold, and the temperature profile was monitored over the curing process.

Heat Release. The heat release was measured using a Differential Photocalorimetry (DPC) Accessory (Model DSC2910, TA Instruments, New Castle, Del.) attached to a Modulated Differential Scanning Calorimeter (DSC) (Model 2920, TA Instruments). Samples were weighed out according to Tables 1(a) and 1(b) and mixed as described above. Approximately 10 mg of the mixture was placed in a DSC pan and the exact weight was recorded. The pan was placed in the DPC and the heat release data were recorded under isothermal conditions (37° C.) for 30 minutes. PMMA heat release was measured by combining the solid and liquid phases of the surgical formulation, weighing a small portion in a DSC pan, and recording the heat release for 30 minutes. The heat release due to crosslinking was calculated as the area under the differential heat release curve divided by the sample weight.

Gel Point. The gel point was determined using a rheometer (Model AR1000, TA Instruments). The gel point is defined as the time corresponding to the formation of an infinite polymer network in which all of the chains are bound together at a minimum of one site. At the gel point, the polymer viscosity change with time asymptotically approaches infinity. For our experiments, the gel point represented the onset of the sudden increase of the complex viscosity ($\eta^*$) of the curing composite paste. Samples were weighed out according to Tables 1(a) and 1(b) and mixed as described above. The suspension was then placed in a Teflon mold 10 mm in diameter and 15 mm in depth attached to the temperature controlled plate of the rheometer (T=37° C.). A cylindrical, stainless steel parallel plate geometry 8 mm in diameter was lowered until it was immersed approximately 1 mm into the polymer solution. An oscillatory program consisting of a time sweep at an oscillatory frequency of 1 Hz and magnitude of 0.5% strain was used to monitor the viscosity as the composite cured. PMMA controls were performed by mixing the liquid and solid phase components at time zero, placing the mixture in the mold, and monitoring the viscosity versus time plot until the material cured. For PMMA, which is a linear polymer, the gel point was defined by analogy as the onset of the sudden increase of the complex viscosity of the curing material.

Mechanical Studies. The P(PF) was dissolved in one-half the total amount of N-VP. The solid phase components (NaCl,$\mu$-TCP) were added, followed by the BP which was dissolved in the remaining N-VP. The resulting paste was placed into cylindrical Teflon molds 6 mm in diameter and 12 mm in height. PMMA control samples were prepared by combining the liquid and solid phase components and pressing the paste into the molds. After a twenty-four hour period, the cylinders were removed and analyzed using an 858 Materials Testing System mechanical testing machine (MTS Systems Corp., Eden Prairie, Minn.) following the guidelines set in ASTM F451-95. Samples were compressed at a crosshead speed of 1 mm/min until failure, with the stress versus strain curve recorded throughout. The compressive modulus was calculated as the slope of the initial stress-strain curve. The compressive strength at yield was defined by drawing a line parallel to the slope defining the modulus, beginning at 1.0% strain; the intersection of this line with the stress-strain curve was recorded as the compressive strength at yield.

Results

The results of the measurements of the five measured properties for each of the eight formulations are set out in Table 2 below, along with the same five properties measured for PMMA. The corresponding factorial analyses for each of the four varied parameters with respect to each of the five measured properties are shown in FIGS. 5A–E, in which the error bars represent the standard error of each effect.

TABLE 2

Summary of results for the eight composite formulations.
Values are given as means ± the standard deviation for each sample set.

| Formulation | Maximum Temperature (° C.) | Heat Release (J/g) | Gel Point (min) | Compressive Strength (MPa) | Compressive Modulus (MPa) |
|---|---|---|---|---|---|
| 1 | 47.7 ± 1.9 | 88.0 ± 2.3 | 8.4 ± 0.3 | 7.3 ± 1.4 | 136.4 ± 28.0 |
| 2 | 39.5 ± 0.8 | 61.2 ± 1.1 | 1.9 ± 0.1 | 4.4 ± 1.7 | 94.1 ± 55.0 |
| 3 | 42.4 ± 4.4 | 78.5 ± 7.1 | 0.8 ± 0.0 | 12.3 ± 1.9 | 264.9 ± 70.0 |
| 4 | 41.5 ± 2.3 | 49.8 ± 6.6 | 9.1 ± 0.2 | 2.9 ± 1.7 | 28.7 ± 9.1 |
| 5 | 39.7 ± 0.8 | 193.6 ± 27.4 | 67.2 ± 0.7 | 9.4 ± 3.4 | 247.0 ± 92.0 |
| 6 | 37.9 ± 0.3 | 193.1 ± 13.1 | 120.5 ± 0.9 | 1.1 ± 0.1 | 23.0 ± 2.6 |
| 7 | 37.7 ± 0.5 | 117.2 ± 1.2 | 120.7 ± 0.8 | 5.8 ± 0.4 | 75.7 ± 13.0 |
| 8 | 39.2 ± 0.6 | 120.4 ± 4.6 | 76.5 ± 9.2 | 12.0 ± 4.0 | 252.8 ± 67.0 |
| PMMA | 94.1 ± 0.2 | 621.0 ± 7.2 | 6.0 ± 0.6 | 45.8 ± 5.2 | 1147.1 ± 239.1 |

Figure 2:
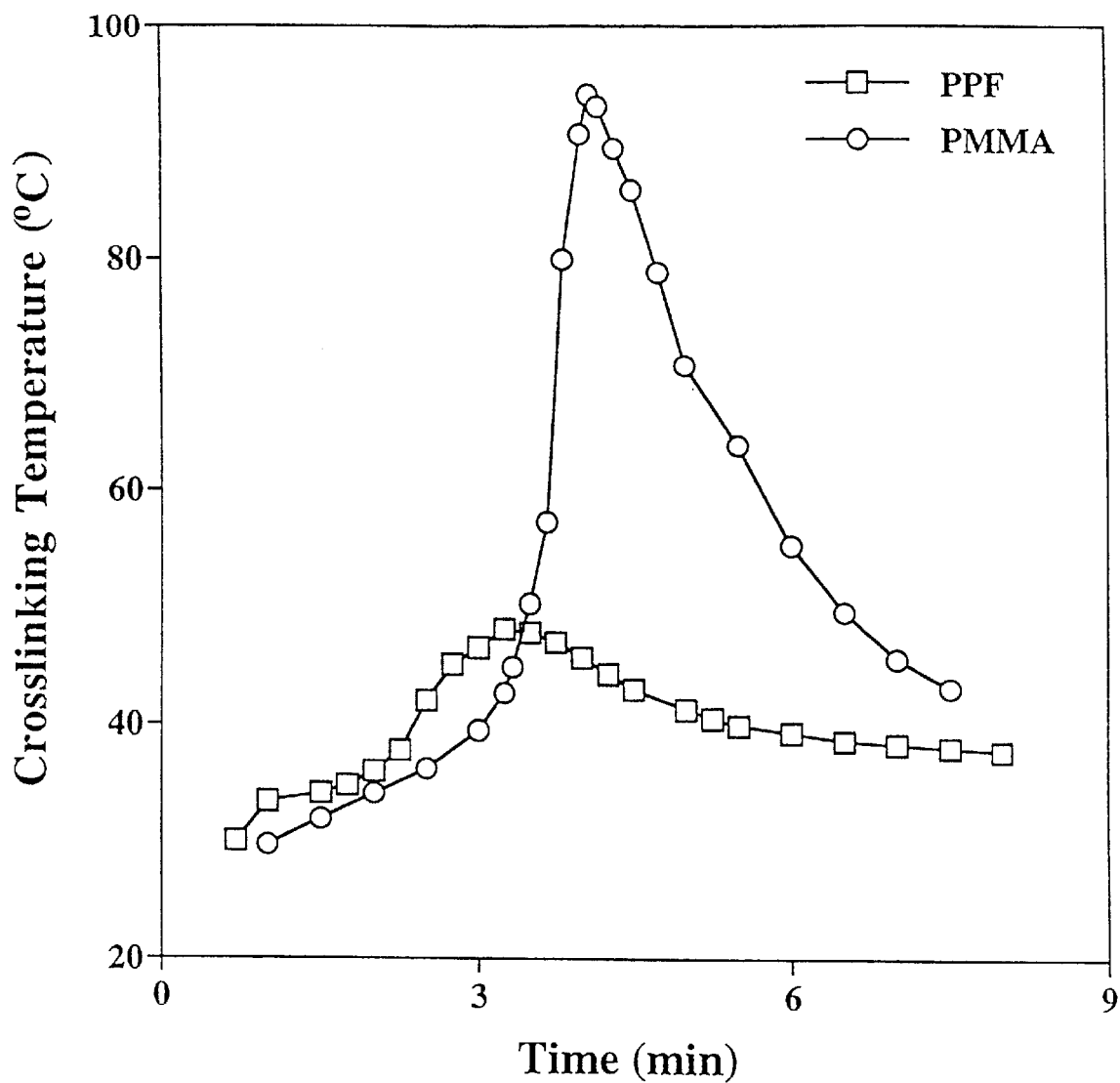
FIG. 2 is a plot of cross-linking temperature vs. time for a representative P(PF) composite formulation and a PMMA control.
Figure 3:
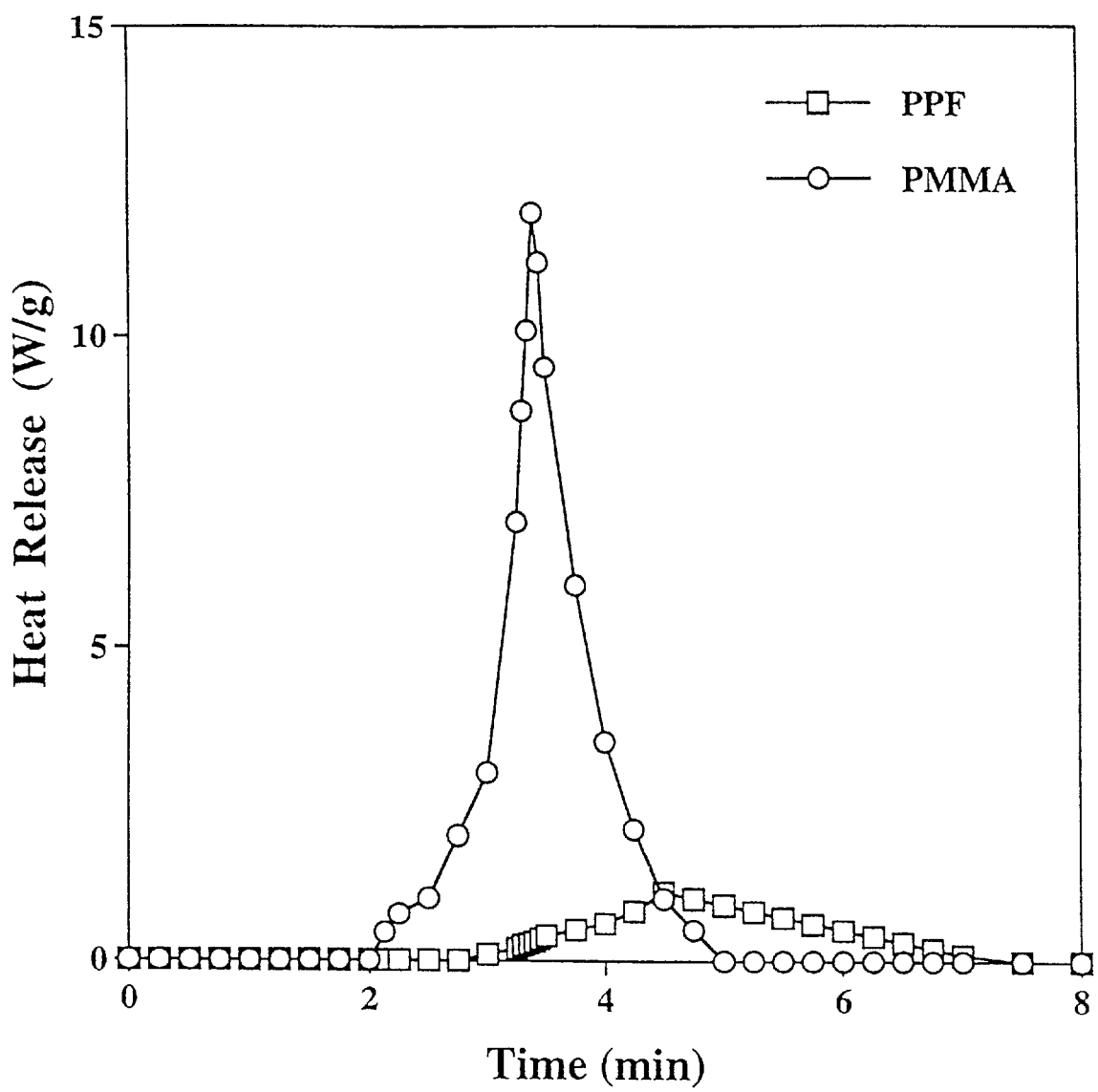
FIG. 3 is a plot of heat release per gram vs. time for a representative P(PF) composite formulation and a PMMA control.

Temperature Profiles. FIG. 2 shows a temperature profile for P(PF) composite formulation 1 and PMMA control. The fractional factorial calculations (FIG. 5A) showed a small variation in maximum crosslinking temperature for different trials; the maximum crosslinking temperatures ranged from 38 to 48° C. The crosslinking temperature was affected most significantly by the polymer molecular weight and porogen weight percent, with an increase in either parameter leading to an increase in the maximum crosslinking temperature (FIG. 3). The effects caused by the amount of monomer and initiator were not significant. PMMA controls had a maximum curing temperature of 94° C.

Figure 5A:
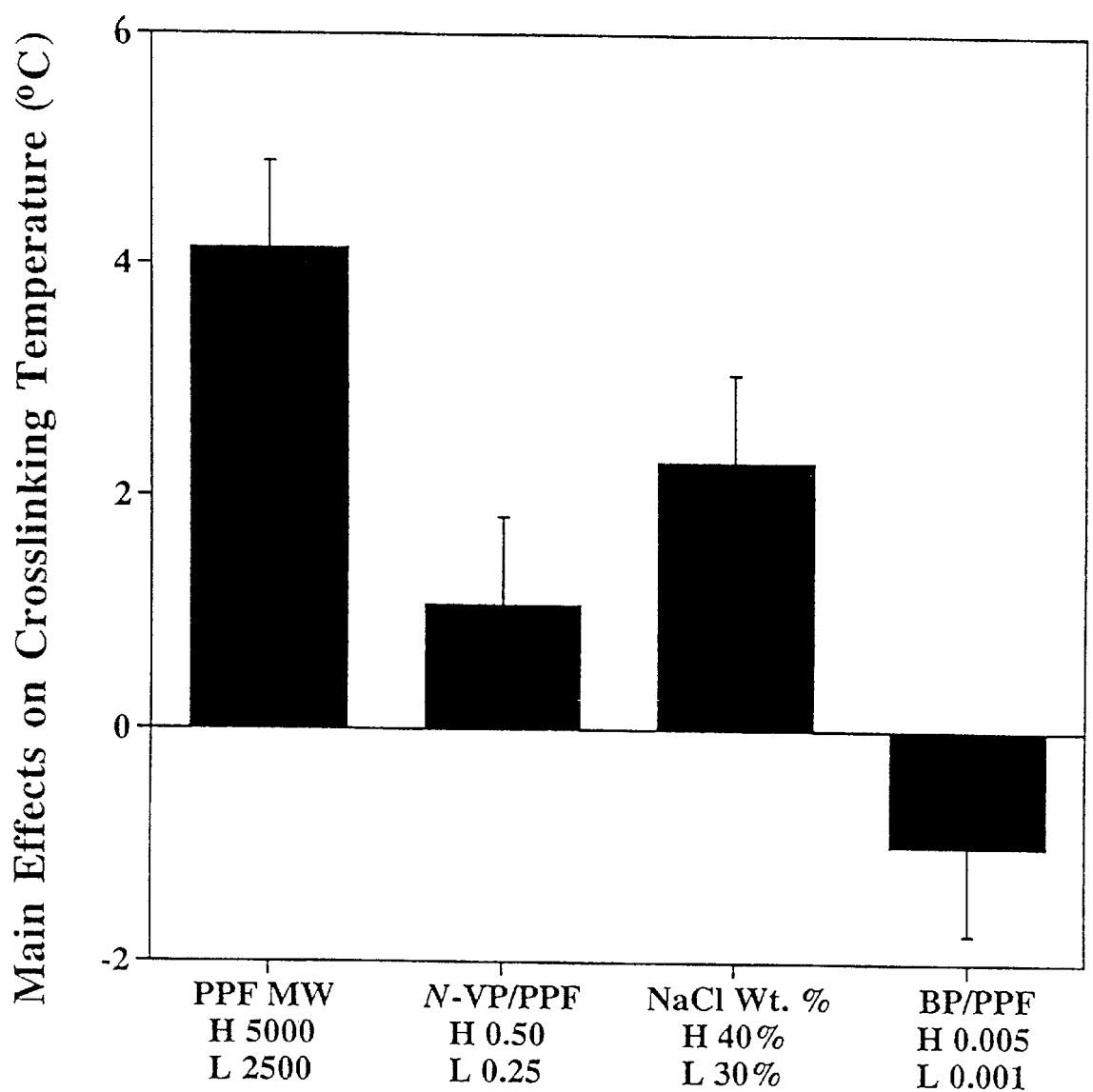
FIGS. 5A–E are graphs showing the relative effects of variations in four factors on cross-linking temperature (FIG. 5A), heat release (FIG. 5B), gel point (FIG. 5C), compressive strength (FIG. 5D), and compressive modulus (FIG. 5E), respectively.
Figure 5B:
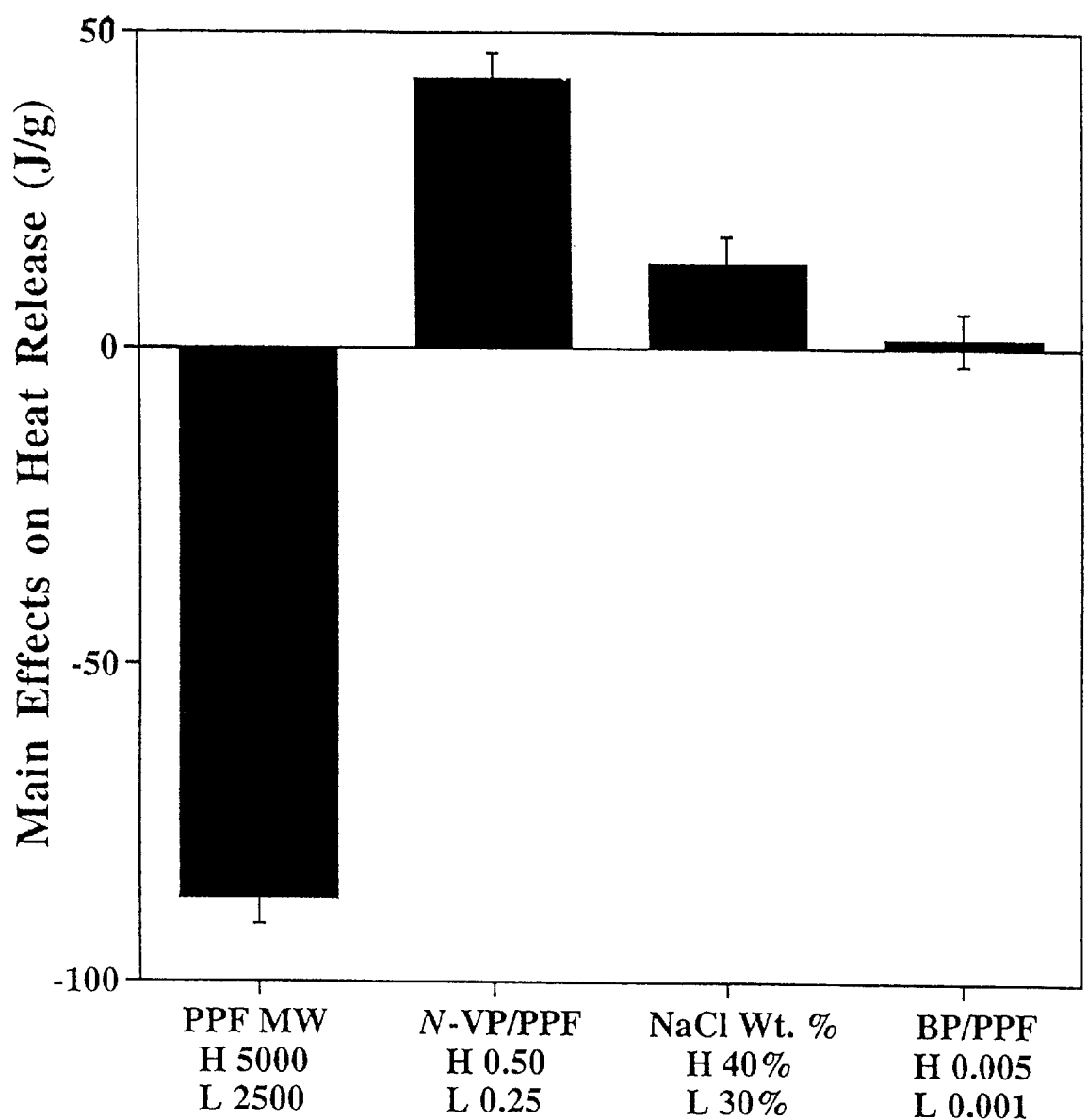

Heat Release. The maximum value for all of the trials was 194 J/g, with a minimum value of 50 J/g (Table 2). In comparison, PMMA controls had a heat release of 621 J/g upon curing. Hence, the P(PF) formulations all released significantly less heat than the PMMA. Heat release thermograms for P(PF) (formulation 1) and PMMA are shown in FIG. 3. The results of the fractional factorial calculations are illustrated in FIG. 5B and were as follows: heat release increases with decreasing molecular weight of P(PF), increasing amount of N-VP, and increasing weight percent of NaCl. The amount of BP in the formulation did not effect the total heat released upon crosslinking.

Figure 4:
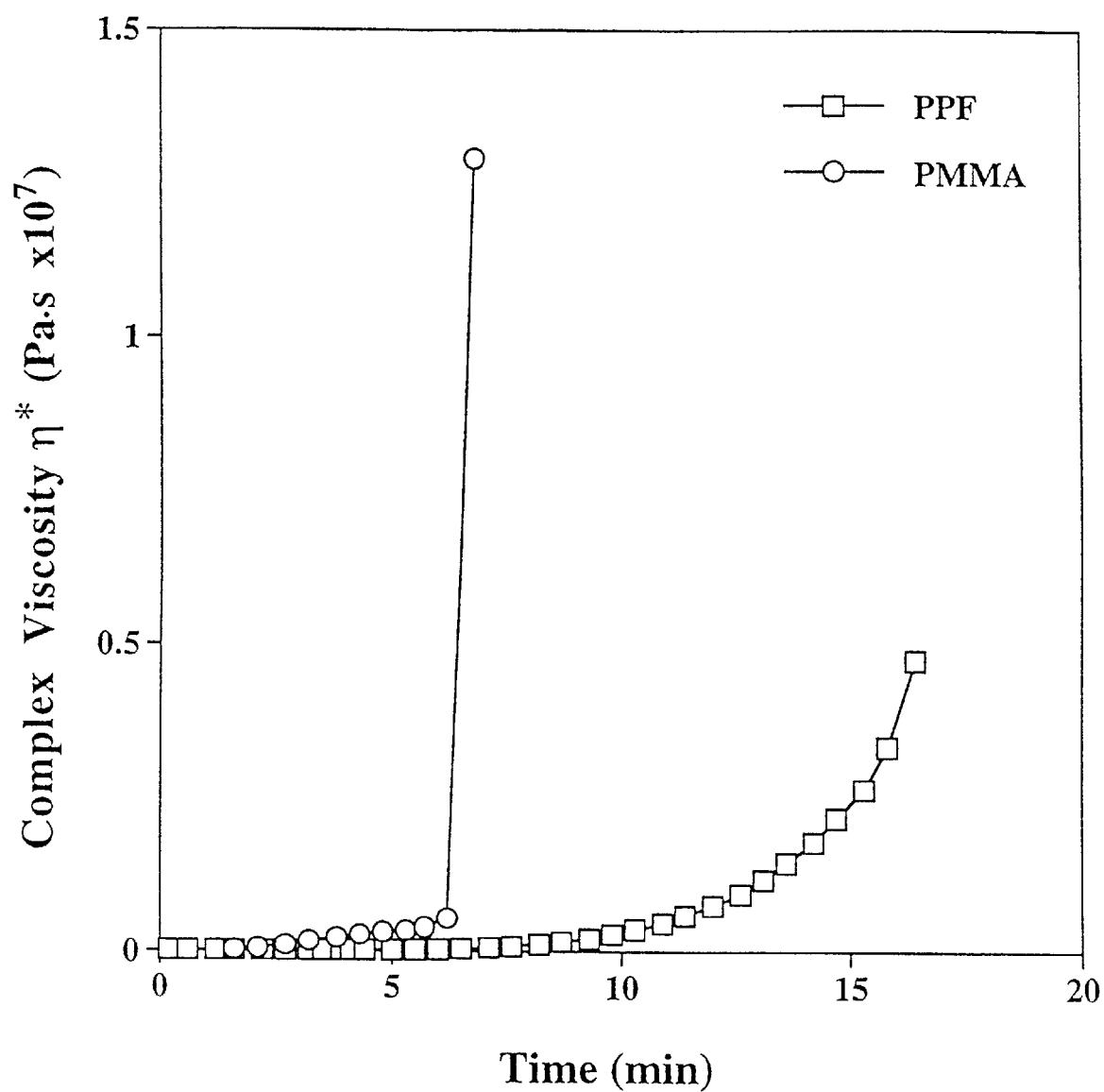
FIG. 4 is a plot of complex viscosity vs. time for a representative P(PF) composite formulation and a PMMA control.
Figure 5C:
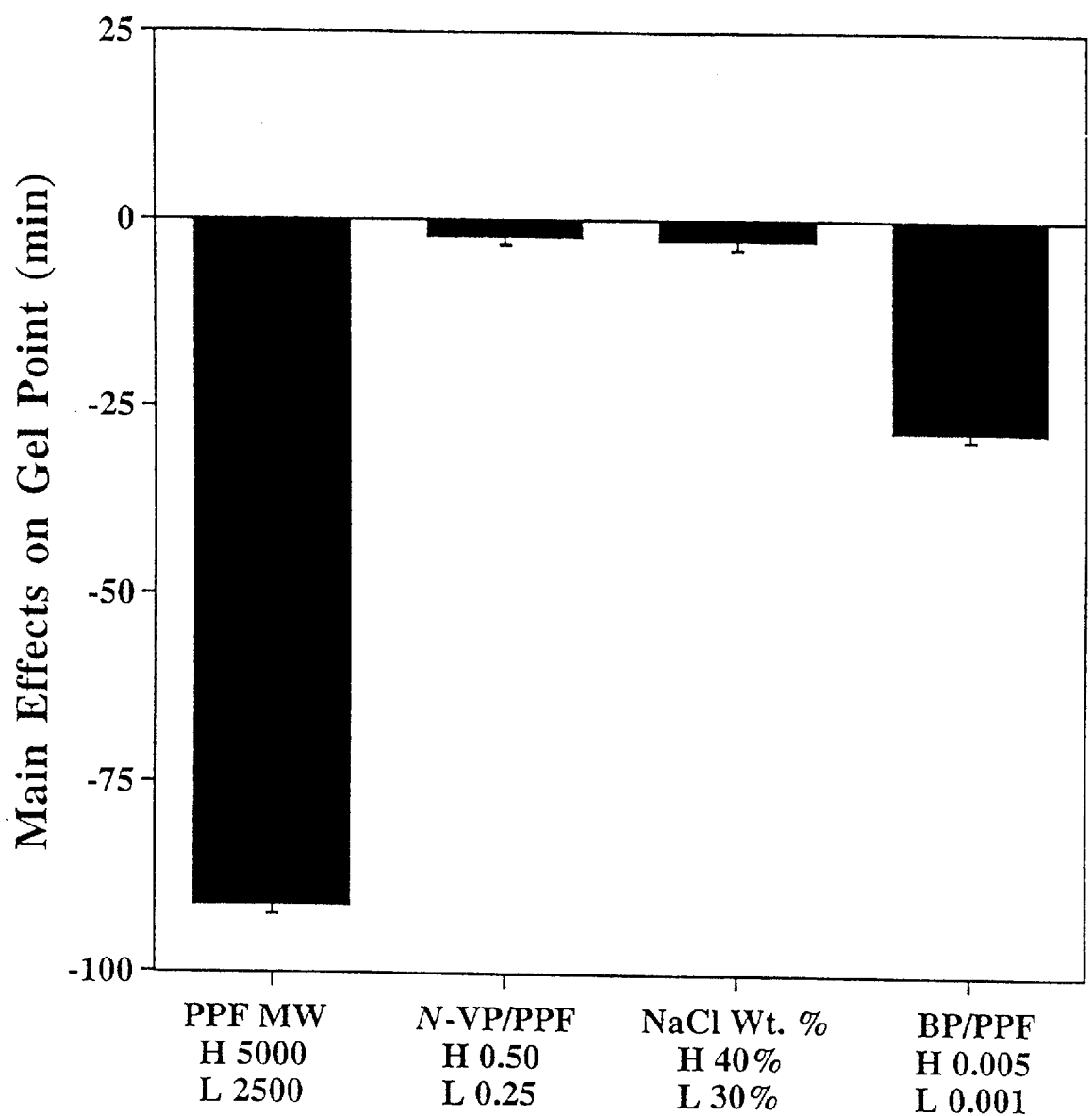

Gel Point. The gel point was varied from 1 to 121 minutes by altering the components according to the fractional factorial design. PMMA controls had a gel point of 6 min. Gel point values for all trials are shown in Table 2. A viscosity versus time plot is shown in FIG. 4 for P(PF) formulation 1 and PMMA. The gel point was most effected by the P(PF) molecular weight, with the amount of benzoyl peroxide also having a significant effect, as illustrated in FIG. 5C. An increase in either of these parameters decreased the time necessary for a sudden increase in the composite viscosity. The monomer concentration and NaCl weight percent did not have a significant effect on the gel point.

Figure 5D:
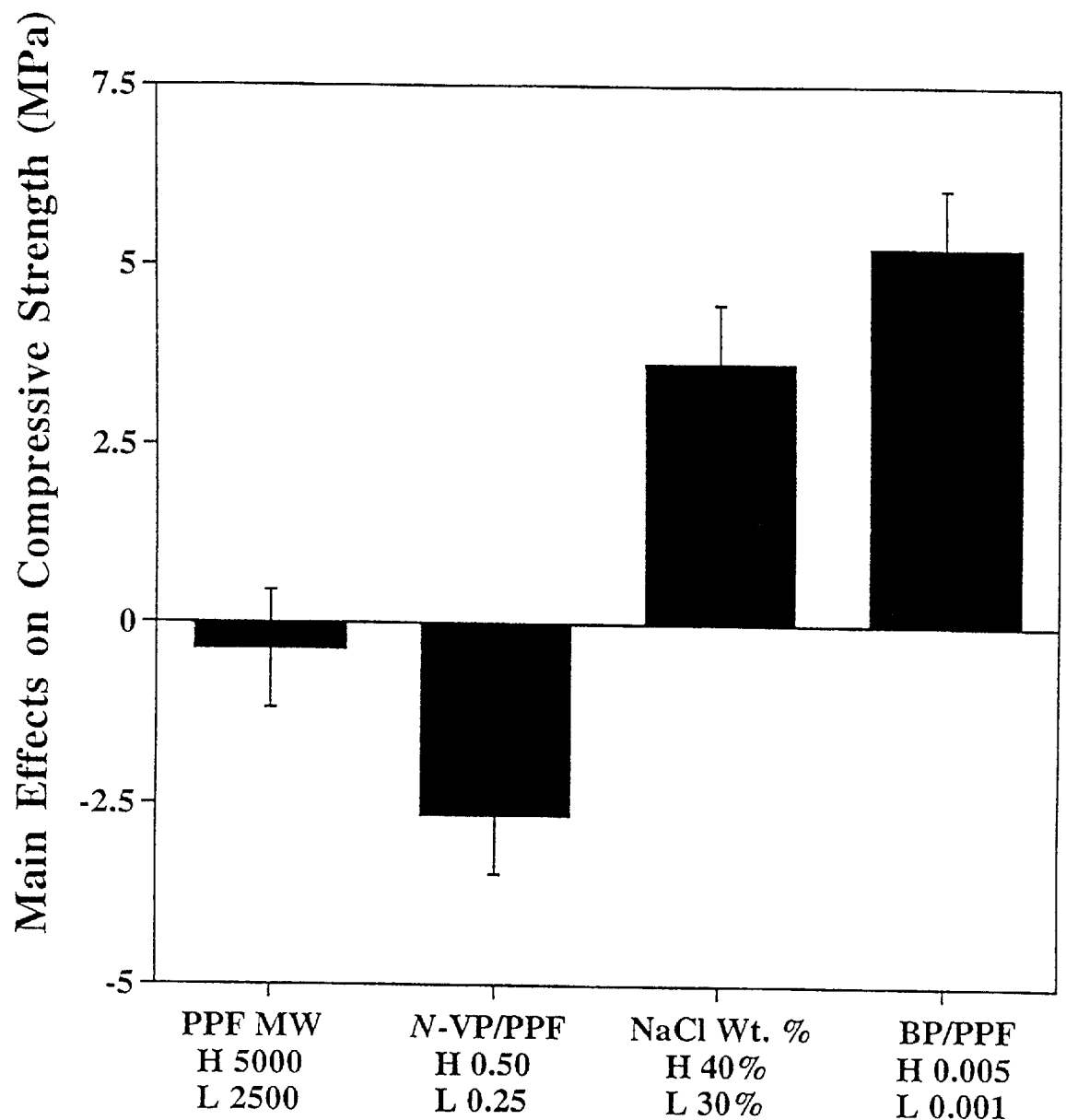
Figure 5E:
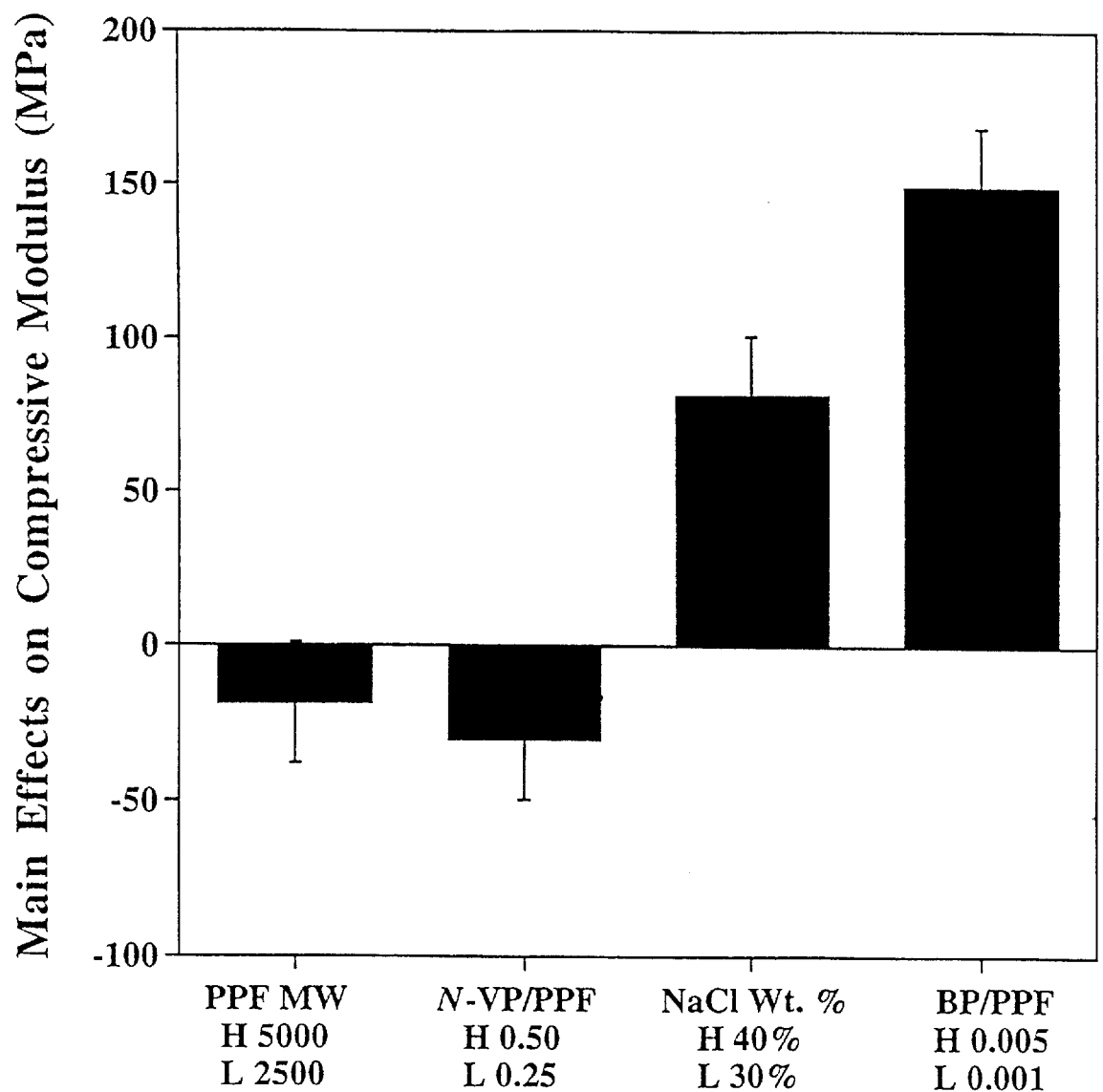

Mechanical Studies. The compressive strength at yield and compressive modulus of the crosslinked composites were measured. As illustrated in FIGS. 5D–E, P(PF) molecular weight did not have a significant effect on either property. An increase in monomer led to a decrease in both compressive strength and modulus, while an increase in NaCl or BP content resulted in an increase in both properties. Absolute values for the formulations varied for compressive strength at yield and compressive modulus of 1 to 12 MPa and 23 to 265 MPa, respectively (Table 2). PMMA controls had a compressive strength at yield of 46 MPa and a compressive modulus of 1147 MPa.

Discussion

The maximum temperatures reached did not vary widely between formulations, with the values ranging from 38 to 48° C. These maximum temperatures should be compared to 94° C., the maximum curing temperature measured for PMMA bone cement. The crosslinking temperature was increased by an increase in either the polymer molecular weight or porogen weight percent. A higher molecular weight created a more viscous solution; the more viscous a polymer solution, the greater the autoacceleration of the polymerization, leading to immediate release of heat. Also, the heat capacity of the composite formulation decreased with the increased NaCl content, thus decreasing the heat transfer rate from the system and increasing the maximum temperature.

The heat release results showed a maximum value for all trials of 194 J/g, with a minimum value of 50 J/g. The fractional factorial calculations showed that the most significant effects were as follows: heat release increases with a decreasing molecular weight of P(PF) and an increasing amount of N-VP. As the molecular weight of P(PF) increases, the chain mobility is restricted and steric hindrances prevent all of the double bonds from being involved in the crosslinking reaction. These restrictions lead to a decrease in heat released throughout the crosslinking with increasing P(PF) molecular weight. The total heat release increased with a higher N-VP content, suggesting that the heat of polymerization of the N-VP monomer is more exothermic than that of P(PF).

The gel point was most effected by the P(PF) molecular weight. As the P(PF) molecular weight increases, the number of crosslinks required to form an infinite network decreases, causing a decrease in the gel point time frame. The amount of benzoyl peroxide effected the time frame of crosslinking as well. An increase in benzoyl peroxide can lead to an accelerated production of free radicals, inducing the formation of poly(N-vinyl pyrrolidinone) (PN-VP) crosslinks and reducing the time necessary for the gel point to occur. By altering the composite formulation, the gel point could be varied from 1 to 121 minutes (the PMMA gel point fell at 6 min). The ability to varying the crosslinking time frame allows the present bone cement to be customized for different orthopaedic applications.

The mechanical properties for many of the composite formulations met design goals of a compressive strength of 5 MPa and compressive modulus of 50 MPa, values that are equivalent to those of human trabecular bone. The composite compressive properties compared favorably to the 46 MPa compressive strength and 1147 MPa compressive modulus for PMMA. As discussed above, the mechanical properties of PMMA are far in excess of those of trabecular bone, and may lead to stress shielding of the bone surrounding the implant site. The values for P(PF)/β-TCP composites more closely approximated the target compressive values for bone substitutes. From the fractional factorial design, it was determined that a decrease in N-VP, an increase in NaCl percent, and an increase in BP all led to an increase in mechanical properties. A decrease in N-VP results in shorter PN-VP crosslinks, which creates a more densely crosslinked polymeric network. Hence, a decrease in N-VP content can lead to an increase in composite mechanical properties. Also, an increase in salt weight percent reinforces the mechanical properties of the composites. Finally, an increase in BP produces shorter PN-VP crosslinks between the P(PF) chains, creating a more tightly crosslinked network and enhancing the mechanical properties of the crosslinked matrix. Hence, the present invention makes it possible to ensure that the mechanical properties of the hardened cement are within optimal ranges, even while other properties, such as gel point, are customized to conform to different application requirements.

The P(PF) molecular weight was not seen to have a significant effect on the mechanical properties. Previous investigations of the mechanical properties of P(PF)/β-TCP composites showed a dependence of the compressive strength and modulus on the P(PF) molecular weight, however, all previous studies were completed using lower molecular weights of P(PF) (600–1200 Da number average molecular weight). It now appears that a threshold molecular weight exists, above which the number of crosslinked double bonds per P(PF) chain is independent of the chain length, and any end effects due to steric hindrances diminish. Although there was no effect of the P(PF) molecular weight on the composite mechanical properties, the P(PF) molecular weight may effect the time course of change in mechanical properties of degrading composites, as previously shown in vitro and in vivo for formulations with lower molecular weight of P(PF).

Through the investigation of the crosslinking characteristics of P(PF) composite formulations, variations in the mixture can be made to optimize the handling properties for different clinical uses and settings. For example, formulation 1 had set times between 5–10 minutes, exhibited crosslinking temperatures much lower than those of PMMA bone cement, and resulted in crosslinked composites with mechanical properties suitable for trabecular bone replacement.

While a preferred embodiment has been disclosed and described, it will be understood that certain modifications could be made without departing from the scope of the present invention. For example, the present method can be used in various other types of tissue augmentation techniques. For example, the present invention can be used in augmentation of hard or soft tissue, as a scaffold for cell transplantion, and/or as a carrier for drugs, including growth factors, angiogenic factors, and tissue involution factors in general. Depending on the application, it will be desirable to optimize both the porogen type and the amount of porogen that is included in the polymer matrix. Suitable porogens include, but are not limited to: sodium citrate, sodium tartrate, gelatins, and carbohydrates. When it is desired to incorporate certain drugs, they can be incorporated directly into the polymer matrix in free form, or can be incorporated as micro- or nano-particles, or can be encapsulated in another material. Similarly, while N-VP was used as the cross-linking agent, it will be understood that the crosslining agent can be any suitable monomer or polymer.

What is claimed is:

1. A method for controlling the gel point of a biocompatible polymeric tissue scaffold containing poly(propylene fumarate), a cross-linking agent, an initiator, and an inorganic filler, comprising:

varying the molecular weight of the poly(propylene fumarate) while maintaining the weight average molecular weight ($M_w$) of the poly(propylene fumarate) above 2000 and the polydispersity index of the poly(propylene fumarate) below 2.

2. The method according to claim 1 wherein the gel point is varied between 1 and 121 minutes while maintaining the compressive strength below 10 MPa.

3. The method according to claim 1 wherein the weight average molecular weight ($M_w$) of the poly(propylene fumarate) is maintained above 4000.

4. The method according to claim 1, further including the step of varying the amount of initiator in the biocompatible polymeric tissue scaffold.

5. The method according to claim 1 wherein the amount of initiator in the biocompatible polymeric tissue scaffold is greater than 0.005 g per gram of poly(propylene fumarate).

6. The method according to claim 1 wherein the amount of initiator in the biocompatible polymeric tissue scaffold is greater than 0.001 g per gram of poly(propylene fumarate).

7. A method for controlling the maximum temperature rise during cross-linking of a biocompatible polymeric tissue scaffold containing poly(propylene fumarate), a cross-linking agent, an initiator, and an inorganic filler, comprising:

varying the molecular weight of the poly(propylene fumarate) while maintaining the weight average molecular weight ($M_w$) of the poly(propylene fumarate) above 2000 and the polydispersity index of the poly(propylene fumarate) below 2.

8. The method according to claim 7 wherein the maximum temperature rise is less than 20° C.

9. The method according to claim 7 wherein the maximum temperature rise is less than 10° C.

10. The method according to claim 7 wherein the weight average molecular weight ($M_w$) of the poly(propylene fumarate) is maintained above 4000.

11. The method according to claim 7 wherein the amount of cross-linking agent in the biocompatible polymeric tissue scaffold is less than 0.5 g per gram of poly(propylene fumarate).

12. The method according to claim 7 wherein the amount of initiator in the biocompatible polymeric tissue scaffold is less than 0.005 g per gram of poly(propylene fumarate).

13. A method for optimizing the mechanical properties and gel time of a biocompatible polymeric tissue scaffold containing poly(propylene fumarate), a cross-linking agent monomer, an inorganic filler, and a radical initiator, comprising:

varying the molecular weight of the poly(propylene fumarate) while maintaining the weight average molecular weight ($M_w$) of the poly(propylene fumarate) above 2000 and the polydispersity index of the poly(propylene fumarate) below 2.

14. The method according to claim 13, further including varying the ratio of initiator to poly(propylene fumarate).

15. The method according to claim 13, further including varying the ratio of monomer to poly(propylene fumarate).

16. The method according to claim 13, further including varying the amount of filler in the bone cement.

17. The method according to claim 13 wherein the weight average molecular weight ($M_w$) of the poly(propylene fumarate) is maintained above 4000.

18. The method according to claim 13 wherein the amount of cross-linking agent in the biocompatible polymeric tissue scaffold is less than 0.5 g per gram of poly(propylene fumarate).

19. A method for optimizing the mechanical properties and gel time of a biocompatible polymeric tissue scaffold containing poly(propylene fumarate), a cross-linking agent monomer, an inorganic filler, and a radical initiator, comprising:

varying the molecular weight of the poly(propylene fumarate) while maintaining the weight average molecular weight ($M_w$) of the poly(propylene fumarate) above 2000 and the polydispersity index of the poly(propylene fumarate) below 2;

varying the ratio of initiator to poly(propylene fumarate); and varying the ratio of monomer to poly(propylene fumarate); and varying the amount of filler in the bone cement.

20. The method according to claim 13 wherein the weight average molecular weight ($M_w$) of the poly(propylene fumarate) is maintained above 4000.

* * * * *